United States Patent
Ouladsmane et al.

(10) Patent No.: US 12,037,318 B1
(45) Date of Patent: Jul. 16, 2024

(54) METHOD OF MAKING A WALL-COATED OPEN TUBULAR CAPILLARY COLUMN WITH A POLY BENZYL STATIONARY PHASE

(71) Applicant: KING SAUD UNIVERSITY, Riyadh (SA)

(72) Inventors: Mohamed Ali Ouladsmane, Riyadh (SA); Ahmed Yacine Badjah Hadj Ahmed, Riyadh (SA); Mohammed Mousa Alshehri, Riyadh (SA); Zeid Abdullah Alothman, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/489,697

(22) Filed: Oct. 18, 2023

(51) Int. Cl.
| | |
|---|---|
| *C07C 7/135* | (2006.01) |
| *B01D 53/02* | (2006.01) |
| *B01J 20/10* | (2006.01) |
| *B01J 20/26* | (2006.01) |
| *B01J 20/28* | (2006.01) |

(52) U.S. Cl.
CPC ............ *C07C 7/135* (2013.01); *B01D 53/025* (2013.01); *B01J 20/103* (2013.01); *B01J 20/262* (2013.01); *B01J 20/28052* (2013.01); *B01D 2253/202* (2013.01); *B01D 2253/25* (2013.01); *B01D 2256/24* (2013.01); *B01D 2257/70* (2013.01); *B01D 2257/7022* (2013.01); *B01D 2257/7027* (2013.01); *B01J 2220/46* (2013.01); *B01J 2220/86* (2013.01)

(58) Field of Classification Search
CPC . B01J 20/10; B01J 20/103; B01J 20/26; B01J 20/261; B01J 20/262; B01J 20/264; B01J 20/265
See application file for complete search history.

(56) References Cited

U.S. PATENT DOCUMENTS

| | | | |
|---|---|---|---|
| 5,098,793 A | 3/1992 | Rohrbach et al. | |
| 2003/0219597 A1 | 11/2003 | Carr et al. | |

FOREIGN PATENT DOCUMENTS

| | | | | |
|---|---|---|---|---|
| EP | 2447715 A1 * | 5/2012 | ............ | B01J 20/286 |
| JP | 2000002697 A * | 1/2000 | ......... | G01N 30/6047 |

OTHER PUBLICATIONS

Schneider et al., Applied Sciences, 2021, 11, 10241. "Qualitative and Quantitative Comparison of Liquid-Liquid Phase Extraction Using Ethyl Acetate and Liquid-Solid Phase Extraction Using Poly-Benzyl-Resin for Natural Products". (Year: 2021).*
Vernon, F. et al., "Aromatic Hydrocarbon Stationary Phases for Gas-Liquid Chromatography", J. of Chromatography A. 86: pp. 17-23 (1973).
Tsonis, Christos P., "Homogeneous Catalytic Polymerization of Benzyl Chloride Leading to Linear High Molecular Weight Polymers: An Elusive Goal" J. Mol. Catalysis 57(3): pp. 313-323 (1990).
Schneider, Yannik K. et al., "Qualitative and Quantitative Comparison of Liquid-Liquid Phase Extraction Using Ethyl Acetate and Liquid-Solid Phase Extraction Using Poly-Benzyl-Resin for Natural Products", Appl. Sci. 11(21):10241 (2021).

* cited by examiner

*Primary Examiner* — Ryan B Huang
(74) *Attorney, Agent, or Firm* — Nath, Goldberg & Meyer; Joshua B. Goldberg (57) ABSTRACT

The method of making a wall-coated open tubular capillary column with a poly benzyl stationary phase is a method of preparing a capillary column for gas chromatography. An inner wall of a fused silica capillary column is cleaned and then rinsed with a sodium hydroxide solution. The fused silica capillary column is flushed with isopropanol to form a pre-treated capillary column, and the pre-treated capillary column is loaded with a mixture of phenyl tri-methoxy silane and alcohol. The loaded pre-treated capillary column is heated to form a treated capillary column, which is then washed. A thin layer of a poly benzyl stationary phase is then coated on the inner wall through condensation polymerization of benzyl chloride monomers with a Lewis acid catalyst in a non-polar solvent.

20 Claims, 9 Drawing Sheets

METHOD OF MAKING A WALL-COATED OPEN TUBULAR CAPILLARY COLUMN WITH A POLY BENZYL STATIONARY PHASE

BACKGROUND

Field

The disclosure of the present patent application relates to gas chromatography, and particularly to a method of making a wall-coated open tubular (WCOT) capillary column for gas chromatography, where the WCOT capillary column has walls coated with a poly benzyl stationary phase.

Description of Related Art

Gas chromatography (GC) is a common type of chromatography used in analytical chemistry for separating and analyzing compounds that can be vaporized without decomposition. Typical uses of GC include testing the purity of a particular substance and separating the different components of a mixture. Gas chromatography involves separating compounds in a mixture by injecting a gaseous or liquid sample into a "mobile phase" (typically called the carrier gas) and passing the gas through a "stationary phase". The mobile phase is usually an inert gas or an unreactive gas, such as helium, argon, nitrogen or hydrogen. The stationary phase can be solid or liquid, although most modern GC systems use a polymeric liquid stationary phase. The stationary phase is contained inside of a separation column. At present, most GC columns are fused silica capillaries with an inner diameter of 100-320 μm and a length of 5-60 m. The GC column is typically located inside an oven where the temperature of the gas can be controlled and the effluent coming off the column is monitored by a suitable detector.

During gas chromatography, the vaporized sample passes through the column, carried by a continuous flow of the mobile phase. Components of the sample pass through the column at different rates, depending on their chemical and physical properties and the resulting interactions with the stationary phase, which lines or fills the column. The column is typically enclosed within a temperature-controlled oven and, as the chemical components exit the end of the column, they are detected and identified electronically.

There are two different types of capillary columns which are presently used in GC: wall-coated open tubular (WCOT) capillary columns and support-coated open tubular (SCOT) capillary columns. WCOT columns are made of a capillary tube which has walls coated with the stationary phase in liquid form. SCOT columns are made using a capillary tube where the inner wall is lined with support material. The stationary phase is adsorbed onto this thin layer of material, so it is present for analysis. WCOT columns are typically the more efficient of the two types of columns.

Typical WCOT capillary columns have walls coated with poly siloxane (and derivatives thereof), polyethylene glycol (and derivatives thereof), ionic liquids and poly ionic liquids as the stationary phase. Although these stationary phases are in common use, none are ideal for GC since some may suffer from low thermal stability, have high molecular weights, be chemically unstable, and are often relatively expensive.

Thus, a method of making a wall-coated open tubular capillary column with a poly benzyl stationary phase solving the aforementioned problems is desired.

SUMMARY

The method of making a wall-coated open tubular capillary column with a poly benzyl stationary phase begins with cleaning the inner wall of a fused silica capillary column with a piranha solution (i.e., concentrated sulfuric acid and hydrogen peroxide in a 3:1 ratio (v/v)), and then washing and drying the capillary column. The capillary column may be washed with bi-distilled water and dried by air stream, as non-limiting examples. The fused silica capillary column can then be rinsed with sodium hydroxide solution (1 M) and left for approximately 30 minutes such that the sodium hydroxide solution activates the silanol groups on the inner wall. The fused silica capillary column can then be washed and dried. The capillary column may be washed with bi-distilled water and air dried, as non-limiting examples. The fused silica capillary column can then be rinsed with hydrochloric acid solution (1 M), and then washed and dried again. The capillary column may be washed with bi-distilled water and air dried, as non-limiting examples. The capillary column can then be flushed with isopropanol to increase the silanol groups on the inner wall, resulting in a pre-treated capillary column.

The pre-treated capillary column can then be treated with phenyl groups to attach the phenyls on the inner wall of the capillary column. The pre-treated capillary column can be loaded with a mixture of phenyl tri-methoxy silane (PhTMS) and one or more alcohols. As a non-limiting example, the pre-treated capillary column may be loaded with a mixture of PhTMS and isopropanol, where the PhTMS has a concentration of about 20% (v/v). The loaded pre-treated capillary column may then be heated at approximately 70° C. for approximately 24 hours, followed by washing with bi-distilled water, isopropanol and toluene, and then drying in air.

The poly benzyl stationary phase can then be coated on the inner wall through condensation polymerization of benzyl chloride monomers with a Lewis acid catalyst in a non-polar solvent. As a non-limiting example, the Lewis acid catalyst may be zinc chloride and the non-polar solvent may be an n-alkane, such as n-undecane. As a further non-limiting example, a concentration of the benzyl chloride monomers in the n-undecane may be between 0.1% and 10% (v/v), and a concentration of the zinc chloride with respect to the benzyl chloride monomers may be 3% (w/w). As a further non-limiting example, a concentration ratio of the benzyl chloride monomers to the zinc chloride to the n-undecane may be 0.1:0.002:99.898 (w/w/w). The above polycondensation method is based on the Friedel-Crafts process, with the polycondensation resulting in the inner wall of the fused silica capillary column being coated with a thin polymeric layer as the immobilized stationary phase.

In an embodiment, the present subject matter relates to a method of making a wall-coated open tubular capillary column with a poly benzyl stationary phase, comprising: cleaning an inner wall of a fused silica capillary column to obtain a cleaned inner wall; rinsing the cleaned inner wall of the fused silica capillary column with a sodium hydroxide solution, followed by rinsing with bi-distilled water, rinsing with a hydrochloric acid solution, and again rinsing with the bi-distilled water to obtain a fused silica capillary column having activated silanol groups; flushing the fused silica capillary column having activated silanol groups with isopropanol to form a pre-treated capillary column; loading the pre-treated capillary column with a mixture of phenyl trimethoxy silane and an alcohol to obtain a loaded pre-treated capillary column having activated silanol groups; heating the loaded pre-treated capillary column having activated silanol groups to form a treated capillary column; washing the treated capillary column; and coating a poly benzyl stationary phase on the inner wall through condensation polymerization of benzyl chloride monomers with a Lewis acid catalyst in a non-polar solvent.

In another embodiment, the present subject matter relates to a wall-coated open tubular capillary column with a poly benzyl stationary phase made according to the methods as described herein.

In a further embodiment, the present subject matter relates to a method of conducting gas chromatography separation of a homologue standard mixture, the method comprising: injecting the homologue standard mixture into an inlet of the wall-coated open tubular capillary column described herein; and separating the homologue standard mixture.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

The method of making a wall-coated open tubular capillary column with a poly benzyl stationary phase begins with cleaning the inner wall of a fused silica capillary column with a piranha solution (i.e., concentrated sulfuric acid and hydrogen peroxide in a 3:1 ratio (v/v)), and then washing and drying the capillary column. The capillary column may be washed with bi-distilled water and dried by air stream, as non-limiting examples. The fused silica capillary column can then be rinsed with sodium hydroxide solution (1 M) and left for approximately 30 minutes such that the sodium hydroxide solution activates the silanol groups on the inner wall. The fused silica capillary column can then be washed and dried. The capillary column may be washed with bi-distilled water and air dried, as non-limiting examples. The fused silica capillary column can then be rinsed with hydrochloric acid solution (1 M), and then washed and dried again. The capillary column may be washed with bi-distilled water and air dried, as non-limiting examples. The capillary column can then be flushed with isopropanol to increase the silanol groups on the inner wall, resulting in a pre-treated capillary column.

The pre-treated capillary column can then be treated with phenyl groups to attach the phenyls on the inner wall of the capillary column. The pre-treated capillary column can be loaded with a mixture of phenyl tri-methoxy silane (PhTMS) and one or more alcohols. As a non-limiting example, the pre-treated capillary column may be loaded with a mixture of PhTMS and isopropanol, where the PhTMS has a concentration of about 20% (v/v). The loaded pre-treated capillary column may then be heated at approximately 70° C. for approximately 24 hours, followed by washing with bi-distilled water, isopropanol and toluene, and then drying in air.

The poly benzyl stationary phase can then be coated on the inner wall through condensation polymerization of benzyl chloride monomers with a Lewis acid catalyst in a non-polar solvent. As a non-limiting example, the Lewis acid catalyst may be zinc chloride and the non-polar solvent may be an n-alkane, such as n-undecane. As a further non-limiting example, a concentration of the benzyl chloride monomers in the n-undecane may be between 0.1% and 10% (v/v), and a concentration of the zinc chloride with respect to the benzyl chloride monomers may be 3% (w/w). As a further non-limiting example, a concentration ratio of the benzyl chloride monomers to the zinc chloride to the n-undecane may be 0.1:0.002:99.898 (w/w/w). The above polycondensation method is based on the Friedel-Crafts process, with the polycondensation resulting in the inner wall of the fused silica capillary column being coated with a thin polymeric layer as the immobilized stationary phase.

In an embodiment, the present subject matter relates to a method of making a wall-coated open tubular capillary column with a poly benzyl stationary phase, comprising: cleaning an inner wall of a fused silica capillary column to obtain a cleaned inner wall; rinsing the cleaned inner wall of the fused silica capillary column with a sodium hydroxide solution, followed by rinsing with bi-distilled water, rinsing with a hydrochloric acid solution, and again rinsing with the bi-distilled water to obtain a fused silica capillary column having activated silanol groups; flushing the fused silica capillary column having activated silanol groups with isopropanol to form a pre-treated capillary column; loading the pre-treated capillary column with a mixture of phenyl trimethoxy silane and an alcohol to obtain a loaded pre-treated capillary column having activated silanol groups; heating the loaded pre-treated capillary column having activated silanol groups to form a treated capillary column; washing the treated capillary column; and coating a poly benzyl stationary phase on the inner wall through condensation polymerization of benzyl chloride monomers with a Lewis acid catalyst in a non-polar solvent.

In an embodiment, the step of cleaning the inner wall of the fused silica capillary column can comprise cleaning and etching the inner wall of the fused silica capillary column with a solution of sulfuric acid and hydrogen peroxide with a 3:1 concentration ratio (v/v).

In another embodiment, the step of flushing the fused silica capillary column having activated silanol groups can increase a total number of the activated silanol groups.

In a further embodiment, the mixture of phenyl tri-methoxy silane and the alcohol can comprise a mixture of phenyl trimethoxy silane and isopropanol, wherein the phenyl tri-methoxy silane can have a concentration of about 20% (v/v).

In an additional embodiment, the step of heating the loaded pre-treated capillary column can comprise heating the loaded pre-treated capillary column for at least about 24 hours at a temperature of about 60° C. to about 80° C., about 65° C. to about 75° C., or about 70° C.

In an embodiment, the treated capillary column can comprise phenyl groups attached to a surface of the activated silanol groups.

In another embodiment, the step of washing the treated capillary column can comprise washing the treated capillary column with bi-distilled water, isopropanol, and toluene.

In a further embodiment, the Lewis acid catalyst can comprise zinc chloride.

In an additional embodiment, the non-polar solvent can comprise an n-alkane. In this regard, the n-alkane can comprise n-undecane.

In an embodiment, a concentration of the benzyl chloride monomers in the non-polar solvent can be between 0.1% and 10% (v/v).

In another embodiment, a concentration of the Lewis acid catalyst with respect to the benzyl chloride monomers can be 3% (w/w). In this regard, a concentration ratio of the benzyl chloride monomers to the Lewis acid catalyst to the non-polar solvent is 0.1:0.002:99.898 (w/w/w).

In another embodiment, the present subject matter relates to a wall-coated open tubular capillary column with a poly benzyl stationary phase made according to the methods as described herein.

In this regard, the wall-coated open tubular capillary column can be configured for use as a gas chromatograph column.

In an additional embodiment, the poly benzyl stationary phase can comprise a crosslinked polymeric thin and uniform layer. In another embodiment in this regard, the crosslinked polymeric thin and uniform layer can be attached to the inner wall of the treated capillary column.

In a further embodiment, the present subject matter relates to a method of conducting gas chromatography separation of a homologue standard mixture, the method comprising: injecting the homologue standard mixture into an inlet of the wall-coated open tubular capillary column described herein; and separating the homologue standard mixture.

In this regard, the homologue standard mixture can comprise a mixture of linear alkanes.

In an additional embodiment, the homologue standard mixture injected into the wall-coated open tubular capillary column can comprise 1 µL and the inlet can be heated at 250° C. with a split ratio of 1:100.

Figure 1A:
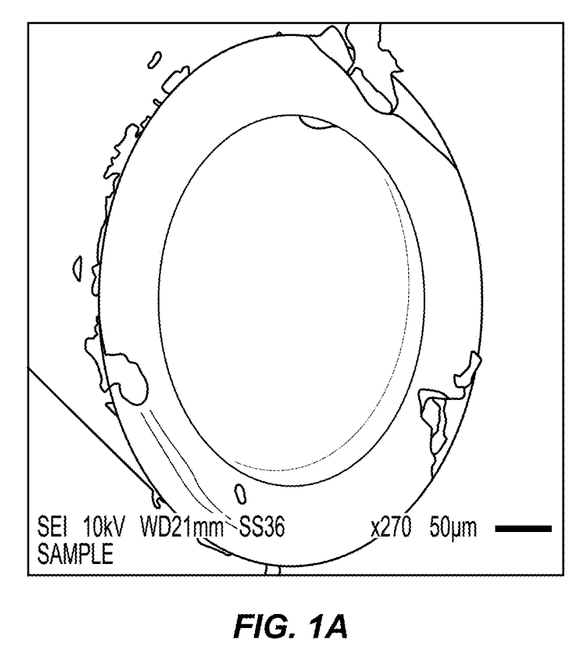
FIG. 1A is a scanning electron microscope (SEM) image of a capillary column prepared according to the method of making a wall-coated open tubular capillary column with a poly benzyl stationary phase with 1% benzyl chloride monomers (v/v).
Figure 1B:
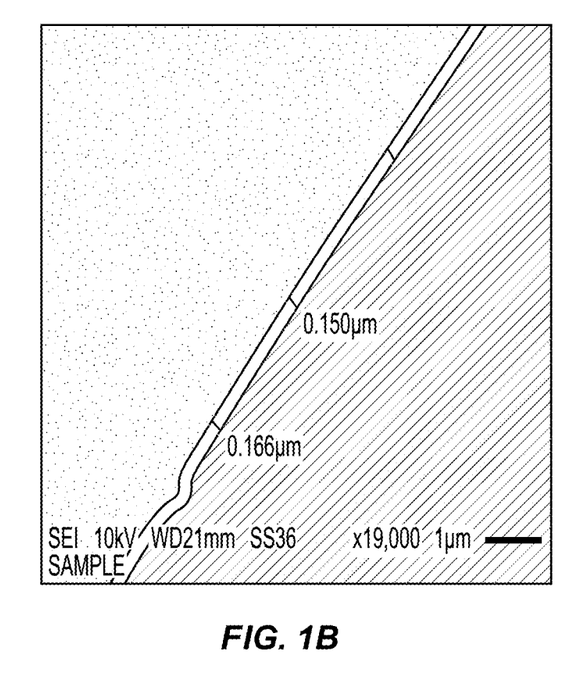
FIG. 1B is a scanning electron microscope (SEM) image of a capillary column prepared according to the method of making a wall-coated open tubular capillary column with a poly benzyl stationary phase with 1% benzyl chloride monomers (v/v).
Figure 1C:
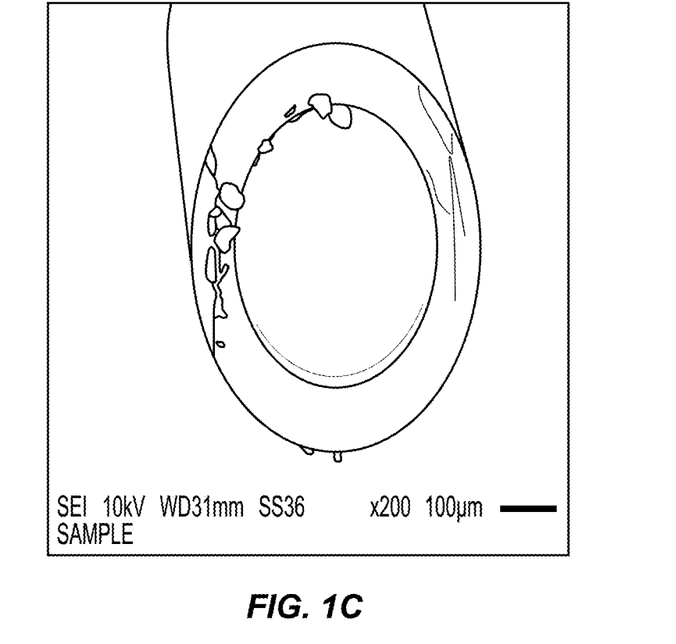
FIG. 1C is a scanning electron microscope (SEM) image of a capillary column prepared according to the method of making a wall-coated open tubular capillary column with a poly benzyl stationary phase with 0.1% benzyl chloride monomers (v/v).
Figure 1D:
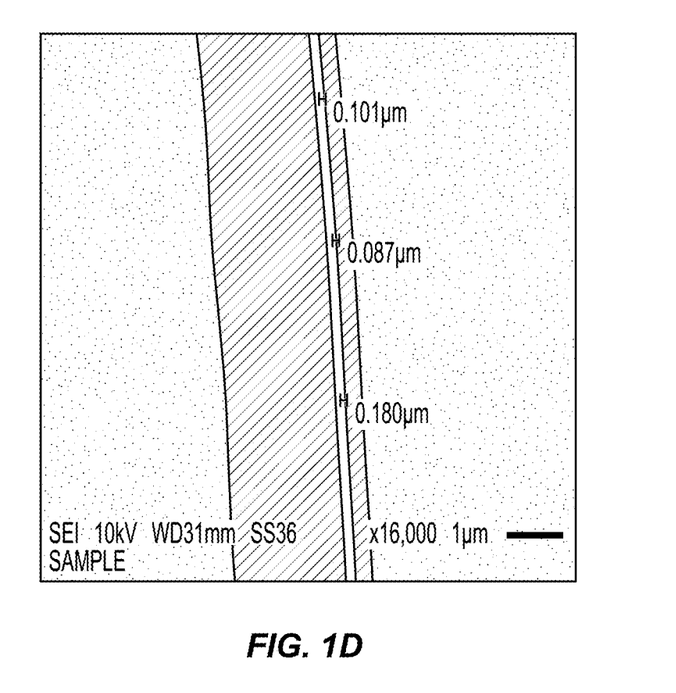
FIG. 1D is a scanning electron microscope (SEM) image of a capillary column prepared according to the method of making a wall-coated open tubular capillary column with a poly benzyl stationary phase with 0.1% benzyl chloride monomers (v/v).

FIGS. 1A and 1B are scanning electron microscope (SEM) images of a capillary column prepared according to the above method with 1% benzyl chloride monomers (v/v), where the prepared column was conditioned at 250° C. for 3 hours. FIGS. 1C and 1D are SEM images of a capillary column similarly prepared, but with 0.1% benzyl chloride monomers (v/v).

Figure 2:
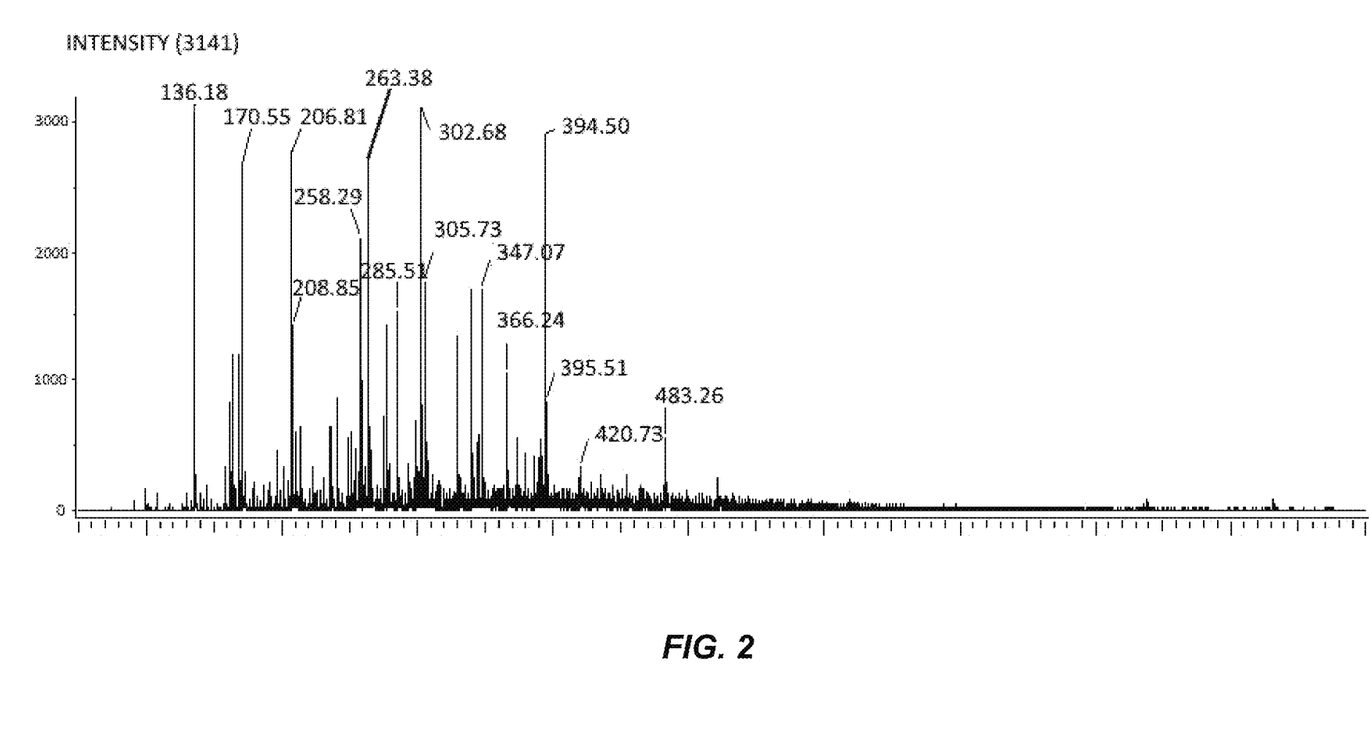
FIG. 2 shows the results of direct analysis of real time coupled with time of flight mass spectroscopy (DART-TOF-MS) of a poly benzyl stationary phase prepared according to the method of making a wall-coated open tubular capillary column with a poly benzyl stationary phase with 0.1% benzyl chloride monomers (v/v).

FIG. 2 shows the results of direct analysis of real time coupled with time of flight mass spectroscopy (DART-TOF-MS) of the poly benzyl stationary phase prepared using 0.1% (w/w) of benzyl chloride monomers. In FIG. 2, the spectra indicate the reaction of benzyl chloride monomers with themselves and oligomers produced during the process.

Figure 3:
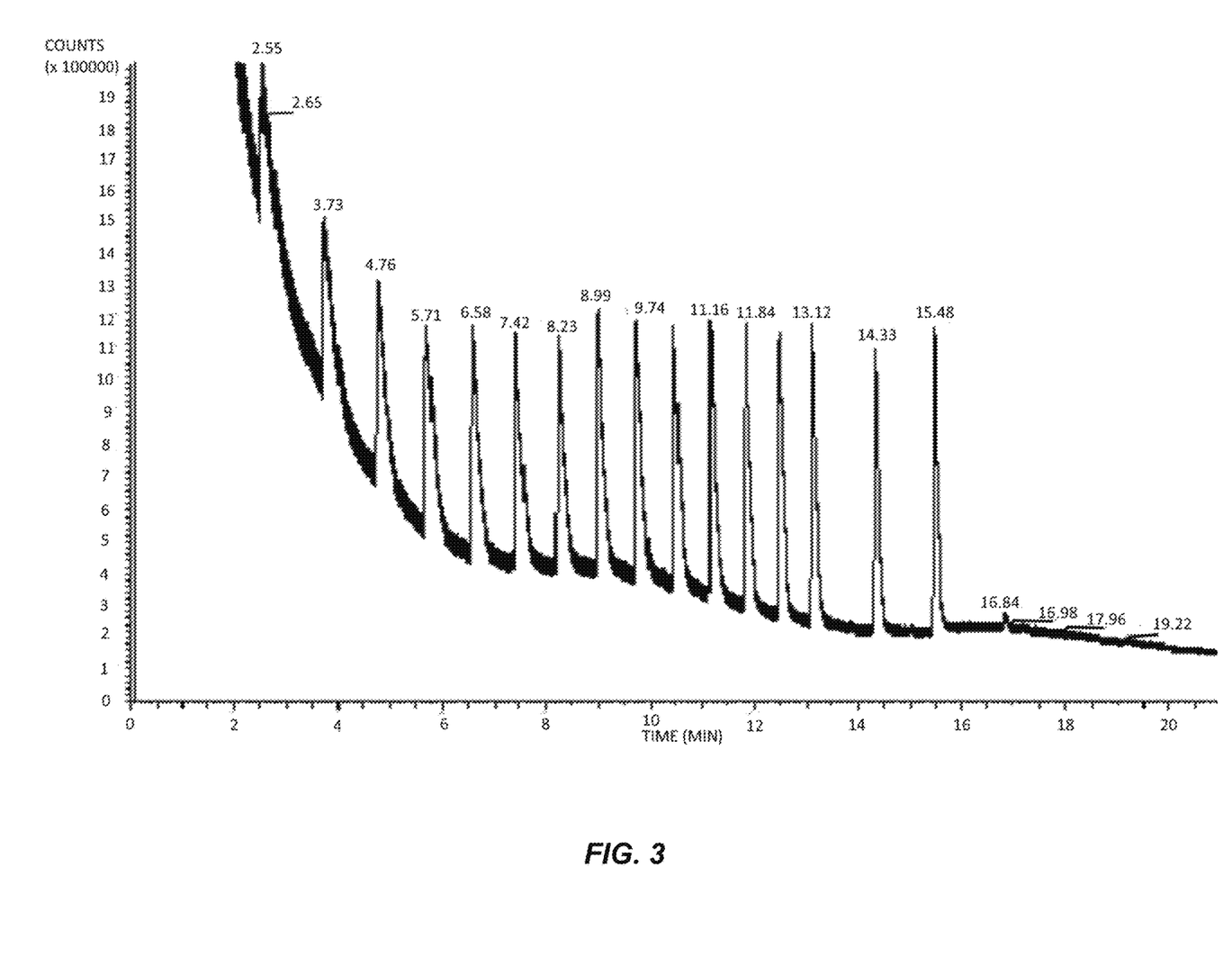
FIG. 3 is a gas chromatograph produced using the wall-coated open tubular capillary column with a poly benzyl stationary phase, where the gas chromatography was performed on a linear saturated alkane mixture.

FIG. 3 is a gas chromatograph produced using the wall-coated open tubular capillary column with a poly benzyl stationary phase, where the gas chromatography was performed on a linear saturated alkane mixture. In this example, the WCOT capillary column had a length of 8 m and an internal diameter of 250 µm and was prepared with 0.1% poly benzyl. The prepared column was conditioned at 250° C. for 3 hours before injection of the sample to be analyzed. The prepared column was used with nitrogen gas as the carrier gas. The carrier gas was supplied at a constant pressure of 100 kPa, and GC was performed using the following GC oven program: 60° C.(2 min) with a ramp of 10° C./min to 200° C. (5 min). A flame ionization detector (FID) at 250° C. was used with nitrogen gas as the makeup gas. The samples were injected in a volume of 1 µL at 250° C. with a split ratio of 100:1. The GC chromatogram of FIG. 3 shows the homologue n-alkanes separation for an exemplary mixture of n-pentadecane, n-hexadecane, n-heptadecane, n-octadecane, n-nonadecane, n-icosane, n-henicosane, n-docosane, n-tricosane, n-tetracosane n-pentacosane, n-hexacosane, n-heptacosane, n-octacosane, n-triacontane, and n-dotriacontane, with a concentration of 100 ppm/n-octane:

|  | Tr min | RSD % | Rs | RSD % | HETP µm | RSD % |
| --- | --- | --- | --- | --- | --- | --- |
| n-Octadecane | 5.72 | 0.27 | — | — | 74.18 | 3.26 |
| n-Nonadecane | 6.60 | 0.23 | 3.12 | 2.15 | 57.45 | 1.33 |
| n-Docosane | 9.04 | 0.71 | — | — | 15.88 | 3.16 |
| n-Tricosane | 9.79 | 0.66 | 3.41 | 0.53 | 18.39 | 7.07 |
| n-Octacosane | 13.14 | 0.22 | — | — | 6.53 | 10.65 |
| n-Triacontane-decane | 14.34 | 0.16 | 6.55 | 2.60 | 4.94 | 4.89 |
| n-Dotriacontane | 15.49 | 0.13 | 5.85 | 3.30 | 5.89 | 9.83 |

Figure 4:
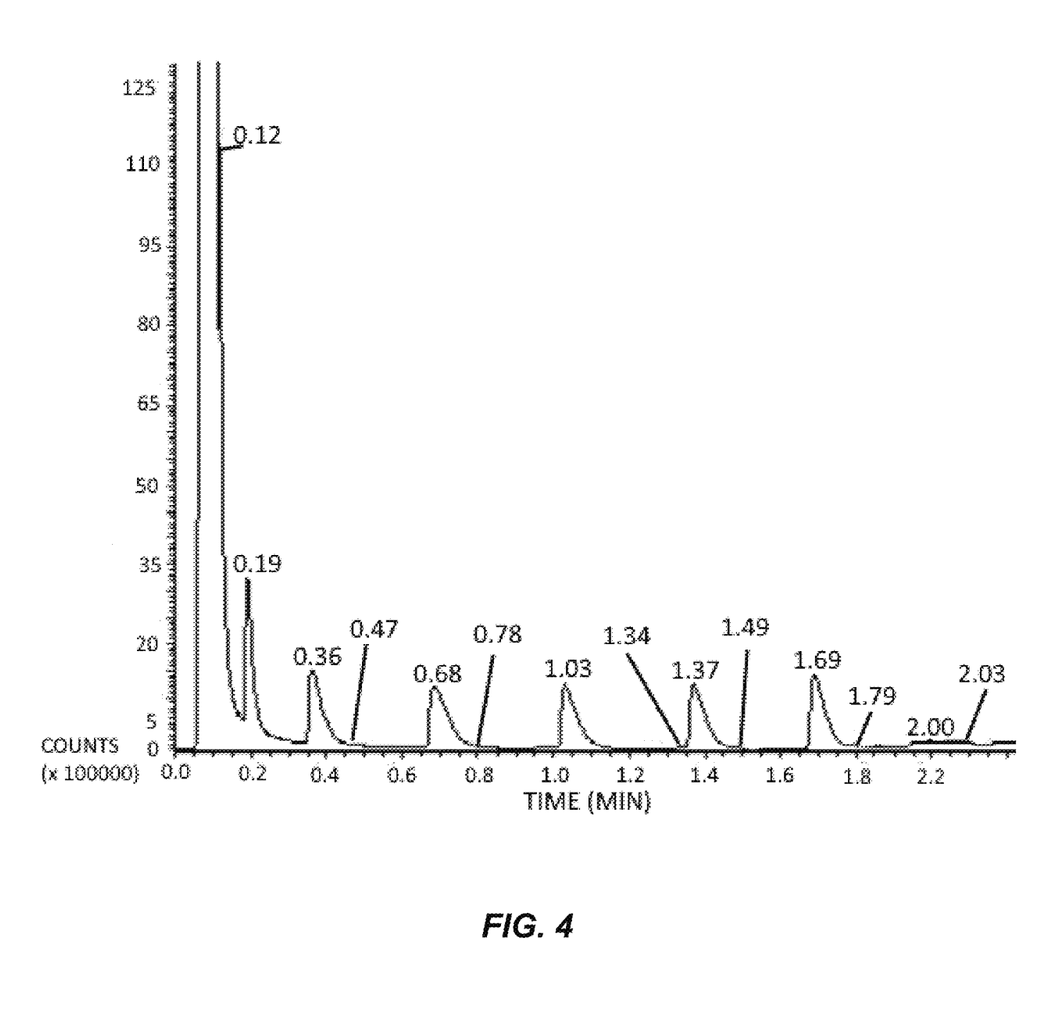
FIG. 4 is a gas chromatograph produced using the wall-coated open tubular capillary column with a poly benzyl stationary phase, where the gas chromatography was performed on a mixture of polycyclic aromatic hydrocarbons.

Another example is shown in FIG. 4, which is a gas chromatograph produced using the wall-coated open tubular capillary column with a poly benzyl stationary phase, where the gas chromatography was performed on polycyclic aromatic hydrocarbons. In this example, the WCOT capillary column was prepared as in the previous example and, during GC, nitrogen gas at a constant pressure of 100 kPa was used as the carrier gas, with the following GC oven program: 60° C.(0.5 min) with a ramp of 30° C./min to 200° C.(5 min). A flame ionization detector (FID) at 250° C. was used with nitrogen gas as the makeup gas. The samples were injected in a volume of 0.2 µL at 250° C. with a split ratio of 500:1. The sample undergoing GC was a mixture of naphthalene, acenaphthene, biphenyl, fluorine, anthracene, phenanthrene, and ter-phenyl, with a concentration of 100 ppm/acetonitrile:

|  | Tr min | RSD % | Rs | RSD % | HETP μm | RSD % |
|---|---|---|---|---|---|---|
| Naphthalene | 0.20 | 5.00 | — | — | 1595 | 13.03 |
| Acenaphthene | 0.37 | 2.70 | 3.18 | 7.46 | 890 | 6.45 |
| Biphenyl | 0.68 | 1.68 | 3.85 | 2.34 | 701 | 3.69 |
| Fluorine | 1.03 | 0.97 | 3.44 | 2.74 | 281 | 0.49 |
| Anthracene | 1.37 | 0.73 | 3.65 | 0.63 | 133 | 1.10 |
| Phenanthrene | 1.69 | 0.59 | 3.66 | 1.30 | 81 | 7.35 |
| Ter-phenyl | 2.01 | 1.32 | 2.21 | 10.65 | 330 | 12.86 |

Figure 5:
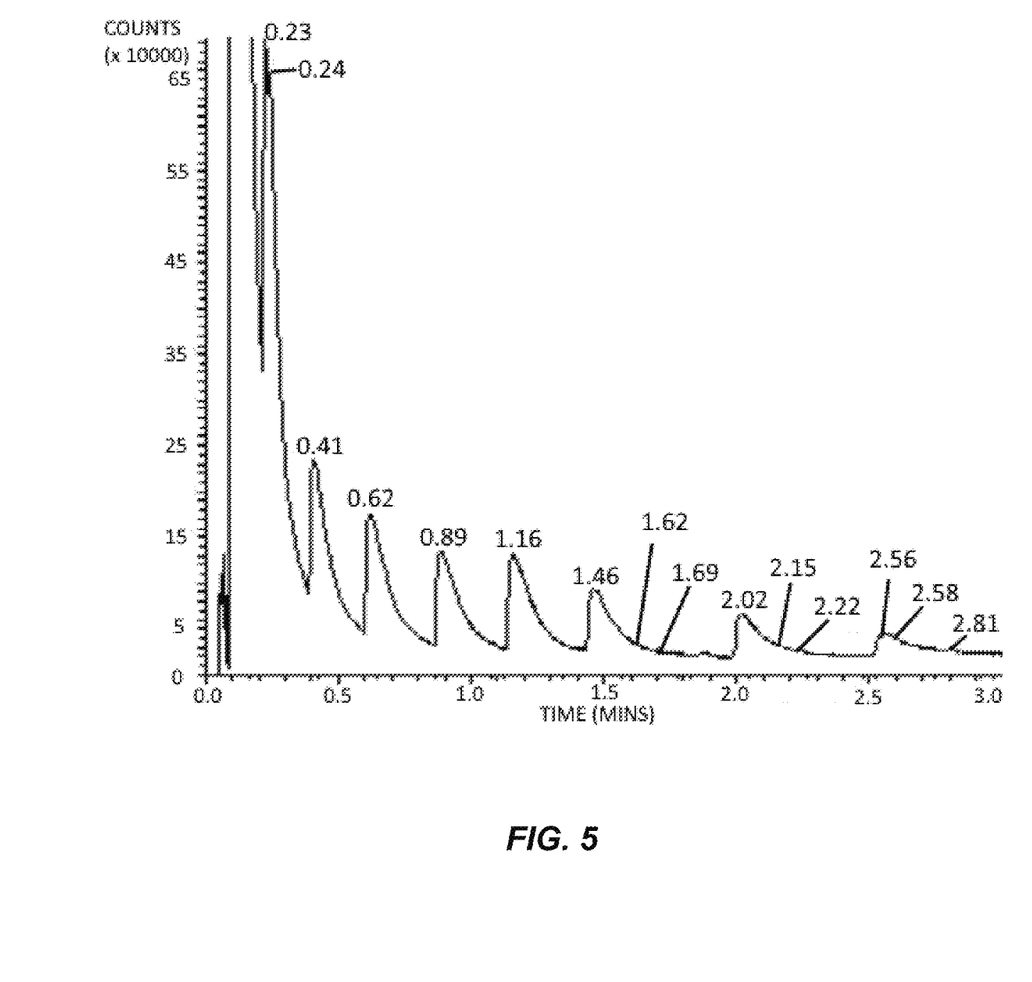
FIG. 5 is a gas chromatograph produced using the wall-coated open tubular capillary column with a poly benzyl stationary phase, where the gas chromatography was performed on a mixture of fatty alcohols.

FIG. 5 is a gas chromatograph produced using the wall-coated open tubular capillary column with a poly benzyl stationary phase, where the gas chromatography was performed on a mixture of fatty alcohols. In this example, the WCOT capillary column was prepared as in the previous examples. During GC, nitrogen gas at a constant pressure of 100 kPa was used as the carrier gas, and the following GC oven program was used: 60° C.(0.5 min) with a ramp of 30° C./min to 200° C.(0.5 min). A flame ionization detector (FID) at 250° C. was used with nitrogen gas as the makeup gas. The samples were injected in a volume of 0.5 μL at 250° C. with a split ratio of 250:1. The mixture was a mixture of n-octanol, 3-octanol, n-nonanol, n-decanol, n-undecanol, n-dodecanol, n-tetradecanol, n-cetyl alcohol, and n-stearyl alcohol, with a concentration of 100 ppm/iso-propanol with heating around 50° C.:

|  | Tr min | RSD % | Rs | RSD % | HETP μm | RSD % |
|---|---|---|---|---|---|---|
| n-Decanol | 0.62 | 1.84 | — | — | 1923 | 7.77 |
| n-Undecanol | 0.88 | 1.12 | 1.61 | 2.12 | 1184 | 6.92 |
| n-Dodecanol | 1.15 | 1.31 | 1.51 | 2.20 | 837 | 1.62 |
| n-Tetradecanol | 1.46 | 0.79 | 1.54 | 2.22 | 620 | 4.65 |
| n-Cetyl alcohol | 2.00 | 0.76 | 2.59 | 4.39 | 373 | 6.88 |
| n-Stearyl alcohol | 2.54 | 0.60 | 2.34 | 3.17 | 277 | 6.15 |

Figure 6:
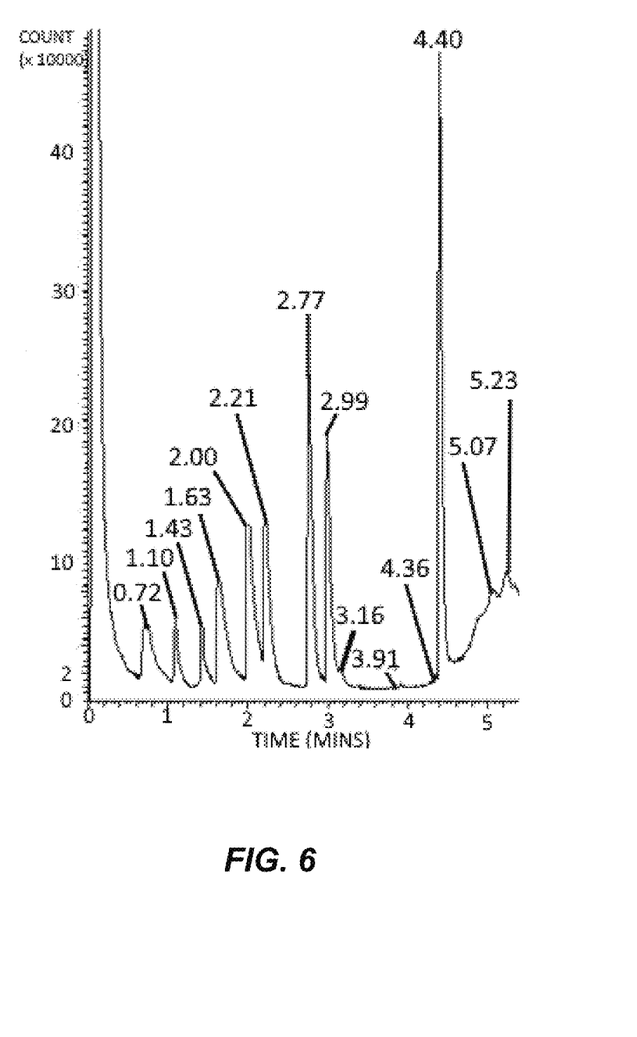
FIG. 6 is a gas chromatograph produced using the wall-coated open tubular capillary column with a poly benzyl stationary phase, where the gas chromatography was performed on a mixture of di-alkyl phthalates.

FIG. 6 is a gas chromatograph produced using the wall-coated open tubular capillary column with a poly benzyl stationary phase, where the gas chromatography was performed on a mixture of di-alkyl phthalates. In this example, the WCOT capillary column was prepared as in the previous examples. During GC, nitrogen gas at a constant pressure of 150 kPa was used as the carrier gas, and the following GC oven program was used: 60° C. (0.5 min) with a ramp of 30° C./min to 200° C.(5 min). A flame ionization detector (FID) at 250° C. was used with nitrogen gas as the makeup gas. The samples were injected in a volume of 0.2 μL at 250° C. with a split ratio of 250:1. The mixture was a mixture of di-methyl phthalate, di-ethyl phthalate, di-iso-propyl phthalate, di-n-propyl phthalate. di-iso-butyl phthalate, di-n-butyl phthalate, and di-n-octyl phthalate, with a concentration of 100 ppm/acetonitrile:

|  | Tr min | RSD % | Rs | RSD % | HETP μm | RSD % |
|---|---|---|---|---|---|---|
| Di-ethyl phthalate | 1.64 | 0.86 | — | — | 802 | 1.87 |
| Di-iso-propyl phthalate | 2.01 | 0.70 | 1.56 | 1.97 | 365 | 14.42 |
| Di-n-propyl phthalate | 2.22 | 0 | 1.19 | 6.36 | 123 | 18.39 |
| Di-iso-butyl phthalate | 2.77 | 0.26 | 4.20 | 8.87 | 62 | 21.79 |
| Di-n-butyl phthalate | 2.99 | 0.24 | 2.00 | 2.91 | 41 | 13.50 |
| Di-n-octyl phthalate | 4.40 | 0 | 13.81 | 1.19 | 15 | 17.61 |

Figure 7:
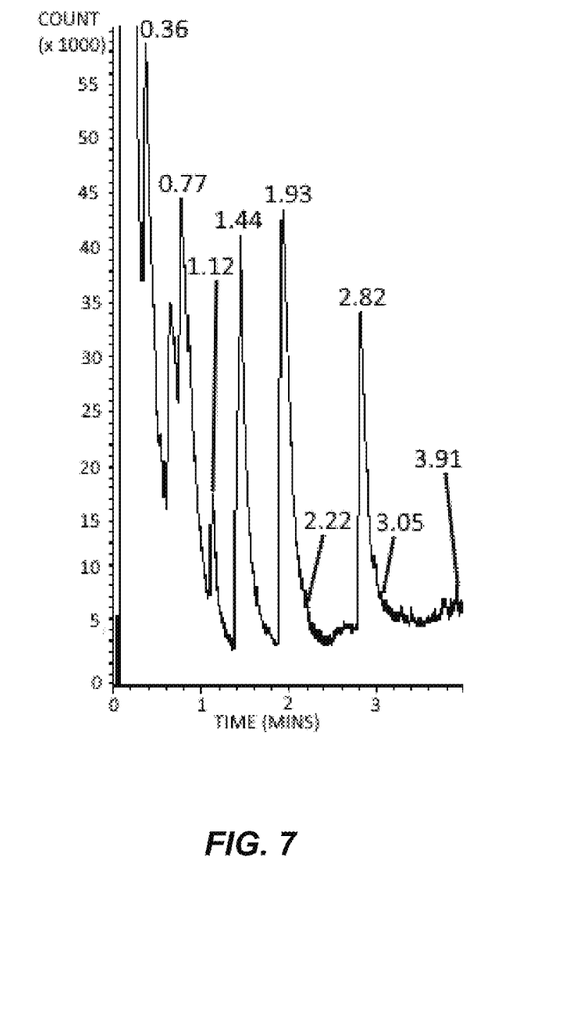
FIG. 7 is a gas chromatograph produced using the wall-coated open tubular capillary column with a poly benzyl stationary phase, where the gas chromatography was performed on a mixture of alkyl phenones.

FIG. 7 is a gas chromatograph produced using the wall-coated open tubular capillary column with a poly benzyl stationary phase, where the gas chromatography was performed on a mixture of alkyl phenones. In this example, the WCOT capillary column was prepared as in the previous examples. During GC, nitrogen gas at a constant pressure of 100 kPa was used as the carrier gas, and the following GC oven program was used: 60° C. (0.5 min) with a ramp of 30° C./min to 200° C. (5 min). A flame ionization detector (FID) at 250° C. was used with nitrogen gas as the makeup gas. The samples were injected in a volume of 0.2 μL at 250° C. with a split ratio of 250:1. The mixture was a mixture of benzoquinone, acetophenone, phenylacetone, butyrophenone, 1,4 naphthaquinone, butyrophenone, benzophenone, and anthraquinone, with a concentration of 100 ppm/acetonitrile:

|  | Tr min | RSD % | Rs | RSD % | HETP μm | RSD % |
|---|---|---|---|---|---|---|
| Butyrophenone | 1.13 | 0.63 | — | — | 410 | 0.69 |
| Naphthaquinone | 1.45 | 0.49 | 2.03 | 3.02 | 533 | 7.86 |
| Benzophenone | 1.93 | 0.38 | 2.35 | 6.28 | 420 | 5.59 |
| Anthraquinone | 2.80 | 1.01 | 3.68 | 6.77 | 262 | 14.02 |

A bleeding test of the polymeric thin layer was performed using a WCOT capillary column prepared as in the previous examples, with nitrogen under a constant pressure of 50 kPa used as a carrier gas, and the following GC oven program was used: 50° C. (0.5 min) with a ramp of 30° C./min to 300° C. (10 min). A flame ionization detector (FID) at 250° C. was used with nitrogen gas as the makeup gas. The immobilized stationary phase prepared from poly benzyl started bleeding at about 290° C. Column bleeding is one of the most common issues in GC, and may be attributed to purity of the carrier gas, air coming from leakage at the injection port, or from leakage at both ends of the column, where contact is made with the injector and the FID detector. This air, and particularly the oxygen therein, may cause damage to the polymeric thin layer.

Figure 8:
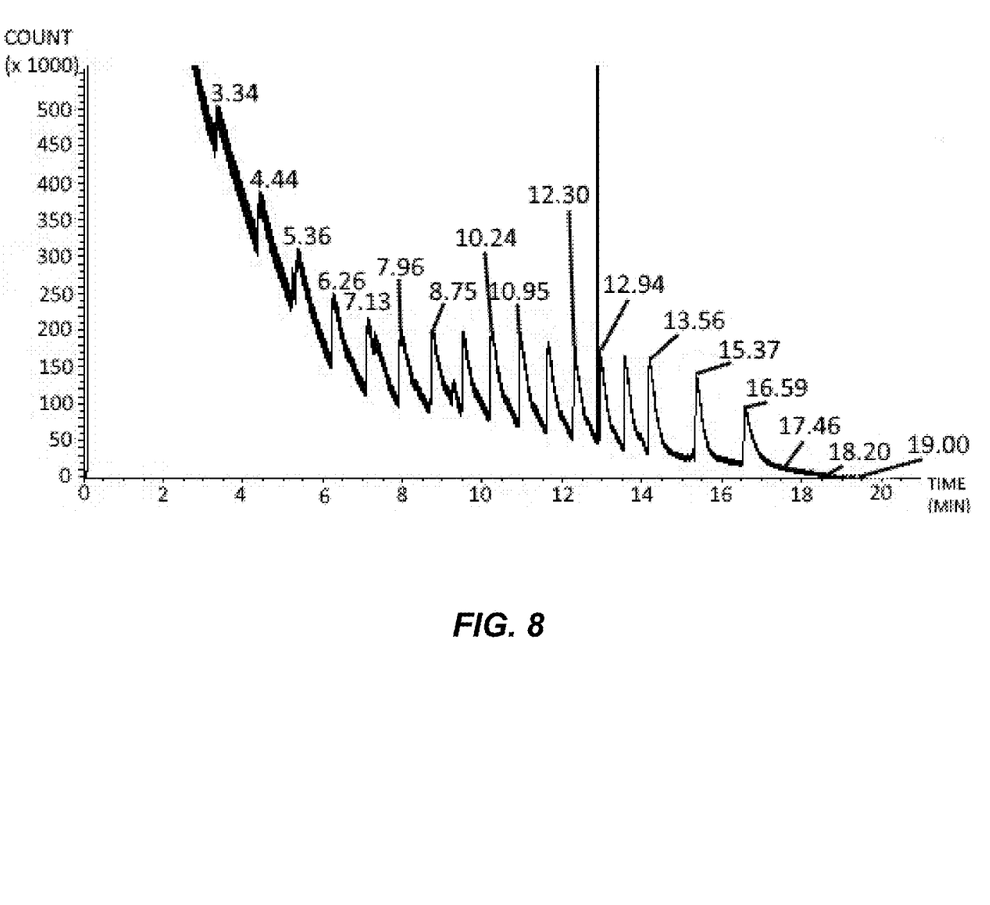
FIG. 8 is a gas chromatograph produced using the wall-coated open tubular capillary column with a poly benzyl stationary phase, following bleed testing thereof, where the gas chromatography was performed on the linear saturated alkane mixture of FIG. 3.

FIG. 8 is a gas chromatograph produced using the wall-coated open tubular capillary column with a poly benzyl stationary phase, following bleed testing thereof, where the gas chromatography was performed on the above exemplary linear saturated alkane mixture of FIG. 3. The same WCOT capillary column as in the example of FIG. 3 was used under the same conditions, but following the bleed testing thereof, and with conditioning at 300° C. for 3 hours before injection of the sample to be analyzed. As shown in FIG. 8, particularly in comparison with FIG. 3, there was a change in the retention time and peak shapes of the compounds.

It is to be understood that the method of making a wall-coated open tubular capillary column with a poly benzyl stationary phase is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A method of making a wall-coated open tubular capillary column with a poly benzyl stationary phase, comprising:
cleaning an inner wall of a fused silica capillary column to obtain a cleaned inner wall;
rinsing the cleaned inner wall of the fused silica capillary column with a sodium hydroxide solution, followed by rinsing with bi-distilled water, rinsing with a hydrochloric acid solution, and again rinsing with the bi-distilled water to obtain a fused silica capillary column having activated silanol groups;
flushing the fused silica capillary column having activated silanol groups with isopropanol to form a pre-treated capillary column;
loading the pre-treated capillary column with a mixture of phenyl trimethoxy silane and an alcohol to obtain a loaded pre-treated capillary column having activated silanol groups;
heating the loaded pre-treated capillary column having activated silanol groups to form a treated capillary column;
washing the treated capillary column; and
coating a poly benzyl stationary phase on the inner wall through condensation polymerization of benzyl chloride monomers with a Lewis acid catalyst in a non-polar solvent.

2. The method of making a wall-coated open tubular capillary column with a poly benzyl stationary phase as recited in claim 1, wherein the step of cleaning the inner wall of the fused silica capillary column comprises cleaning and etching the inner wall of the fused silica capillary column with a solution of sulfuric acid and hydrogen peroxide with a 3:1 concentration ratio (v/v).

3. The method of making a wall-coated open tubular capillary column with a poly benzyl stationary phase as recited in claim 1, wherein the step of flushing the fused silica capillary column having activated silanol groups increases a total number of the activated silanol groups.

4. The method of making a wall-coated open tubular capillary column with a poly benzyl stationary phase as recited in claim 1, wherein the mixture of phenyl trimethoxy silane and the alcohol comprises a mixture of phenyl trimethoxy silane and isopropanol, wherein the phenyl tri-methoxy silane has a concentration of 20% (v/v).

5. The method of making a wall-coated open tubular capillary column with a poly benzyl stationary phase as recited in claim 1, wherein the step of heating the loaded pre-treated capillary column comprises heating the loaded pre-treated capillary column for at least about 24 hours at a temperature of about 70° C.

6. The method of making a wall-coated open tubular capillary column with a poly benzyl stationary phase as recited in claim 1, wherein the treated capillary column comprises phenyl groups attached to a surface of the activated silanol groups.

7. The method of making a wall-coated open tubular capillary column with a poly benzyl stationary phase as recited in claim 1, wherein the step of washing the treated capillary column comprises washing the treated capillary column with bi-distilled water, isopropanol, and toluene.

8. The method of making a wall-coated open tubular capillary column with a poly benzyl stationary phase as recited in claim 1, wherein the Lewis acid catalyst comprises zinc chloride.

9. The method of making a wall-coated open tubular capillary column with a poly benzyl stationary phase as recited in claim 1, wherein the non-polar solvent comprises an n-alkane.

10. The method of making a wall-coated open tubular capillary column with a poly benzyl stationary phase as recited in claim 9, wherein the n-alkane comprises n-undecane.

11. The method of making a wall-coated open tubular capillary column with a poly benzyl stationary phase as recited in claim 1, wherein a concentration of the benzyl chloride monomers in the non-polar solvent is between 0.1% and 10% (v/v).

12. The method of making a wall-coated open tubular capillary column with a poly benzyl stationary phase as recited in claim 1, wherein a concentration of the Lewis acid catalyst with respect to the benzyl chloride monomers is 3% (w/w).

13. The method of making a wall-coated open tubular capillary column with a poly benzyl stationary phase as recited in claim 1, wherein a concentration ratio of the benzyl chloride monomers to the Lewis acid catalyst to the non-polar solvent is 0.1:0.002:99.898 (w/w/w).

14. A wall-coated open tubular capillary column with a poly benzyl stationary phase made according to the method of claim 1.

15. A wall-coated open tubular capillary column with a poly benzyl stationary phase made according to the method of claim 1, wherein the wall-coated open tubular capillary column is configured for use as a gas chromatograph column.

16. The wall-coated open tubular capillary column with a poly benzyl stationary phase of claim 15, wherein the poly benzyl stationary phase comprises a crosslinked polymeric thin and uniform layer.

17. The wall-coated open tubular capillary column with a poly benzyl stationary phase of claim 16, wherein the crosslinked polymeric thin and uniform layer is attached to the inner wall of the treated capillary column.

18. A method of conducting gas chromatography separation of a homologue standard mixture, the method comprising:
injecting the homologue standard mixture into an inlet of the wall-coated open tubular capillary column of claim 15; and
separating the homologue standard mixture.

19. The method of conducting gas chromatography separation of a homologue standard mixture of claim 18, wherein the homologue standard mixture comprises a mixture of linear alkanes.

20. The method of conducting gas chromatography separation of the homologue standard mixture of claim 18, wherein the homologue standard mixture injected into the inlet of the wall-coated open tubular capillary column comprises 1 µL linear alkanes, with a split ratio of 1:100, and the inlet is heated at 250° C.

* * * * *